(12) United States Patent
Hirsch

(10) Patent No.: US 9,770,310 B2
(45) Date of Patent: Sep. 26, 2017

(54) ORTHODONTIC SELF-LIGATING BRACKET

(71) Applicant: PBD, Patent & Business Development AG, Zug (CH)

(72) Inventor: Markus Hirsch, Klagenfurt-Viktring (AT)

(73) Assignee: PBD, Patent & Business Development AG, Zug (CH)

( * ) Notice: Subject to any disclaimer, the term of this patent is extended or adjusted under 35 U.S.C. 154(b) by 0 days.

(21) Appl. No.: 15/053,514

(22) Filed: Feb. 25, 2016

(65) Prior Publication Data
US 2017/0245963 A1    Aug. 31, 2017

(51) Int. Cl.
| A61C 7/30 | (2006.01) |
| A61C 7/02 | (2006.01) |
| A61C 7/28 | (2006.01) |
| A61C 7/34 | (2006.01) |

(52) U.S. Cl.
CPC .............. *A61C 7/30* (2013.01); *A61C 7/02* (2013.01); *A61C 7/287* (2013.01); *A61C 7/34* (2013.01)

(58) Field of Classification Search
CPC .. A61C 7/30; A61C 7/02; A61C 7/287; A61C 7/34
USPC .......................................... 433/8, 11
See application file for complete search history.

(56) References Cited

U.S. PATENT DOCUMENTS

| 3,772,787 A | 11/1973 | Hanson |
| 4,248,588 A | 2/1981 | Hanson |
| 4,492,573 A | 1/1985 | Hanson |
| 4,838,787 A * | 6/1989 | Lerner ................... A61C 7/143 |
| | | 433/14 |
| 5,586,882 A | 12/1996 | Hanson |
| 5,857,850 A | 1/1999 | Voudouris |
| 5,906,486 A | 5/1999 | Hanson |
| 6,368,105 B1 | 4/2002 | Voudouris et al. |
| 6,776,613 B2 | 8/2004 | Orikasa |
| 7,442,039 B2 | 10/2008 | Opin et al. |

(Continued)

FOREIGN PATENT DOCUMENTS

| CN | 201 453 387 U | 5/2010 |
| KR | 101 489 625 B1 | 2/2015 |
| WO | 2014/059053 A2 | 4/2014 |

OTHER PUBLICATIONS

International Search Report and the Written Opinion of the International Searching Authority dated Apr. 28, 2017 in PCT/EP2017/054262.

*Primary Examiner* — Nicholas Lucchesi
(74) *Attorney, Agent, or Firm* — Collard & Roe, P.C.

(57) ABSTRACT

An orthodontic bracket has a base configured for attachment to a tooth surface, a bracket element with an arch wire slot attached to one side of the base, and a clip for securing the arch wire in the slot. The bracket element has a wall portion extending upward along one side of the arch wire slot. This wall portion has three indentations in a line parallel to the mesiodistal direction. There is a channel running entirely through the bracket element underneath the arch wire slot. The clip is substantially U-shaped and has three parallel protrusions shaped to fit within the three indentations of the wall portion, and a locking element. The clip is securable to the bracket by placing the clip through the channel and engaging the locking element onto the bracket element, and placing the protrusions into the indentations of the bracket element.

7 Claims, 4 Drawing Sheets

(56) References Cited

U.S. PATENT DOCUMENTS

| | | | |
|---|---|---|---|
| 7,717,706 B2 | 5/2010 | Foerster | |
| 2003/0031975 A1* | 2/2003 | Voudouris | A61C 7/12 433/8 |
| 2004/0170942 A1* | 9/2004 | Heiser | A61C 7/28 433/11 |
| 2005/0239012 A1* | 10/2005 | Bathen | A61C 7/287 433/10 |
| 2007/0160949 A1* | 7/2007 | Voudouris | A61C 7/28 433/8 |
| 2009/0170049 A1* | 7/2009 | Heiser | A61C 7/285 433/11 |
| 2010/0261131 A1* | 10/2010 | Ruiz-Vela | A61C 7/303 433/10 |
| 2010/0285421 A1* | 11/2010 | Heiser | A61C 7/285 433/11 |
| 2013/0171579 A1 | 7/2013 | Orikasa et al. | |
| 2013/0236847 A1 | 9/2013 | Shin | |
| 2014/0212828 A1* | 7/2014 | Falcone | A61C 7/14 433/11 |
| 2014/0272753 A1* | 9/2014 | Sommer | A61C 7/30 433/11 |
| 2016/0135929 A1 | 5/2016 | Sommer et al. | |

* cited by examiner

ORTHODONTIC SELF-LIGATING BRACKET

BACKGROUND OF THE INVENTION

1. Field of the Invention

This invention relates to a self-ligating orthodontic bracket. In particular, the invention relates to an orthodontic bracket that has a particular three-pronged configuration that makes it easy to assemble yet remains securely fastened under tension.

2. The Prior Art

Self-ligating orthodontic brackets were developed to eliminate the need to secure the arch wire to the bracket with rubber bands. These brackets have a slot to receive the arch wire, and a clip is then snapped into place over the slot to keep the arch wire attached.

U.S. Pat. No. 3,772,787 to Hanson discloses an early design of an active self-ligating bracket based on a flexible clip. New orthodontic brackets each comprise a body slotted for the reception of an arch wire and a U-shaped clip for retaining the arch wire in the slot. The clip is preferably of flat metal conforming to the shape of the body and is movable between two positions in which the slot labial opening is respectively open and closed. A big drawback of this original design is there is nothing to secure the free end of the clip's labial side and therefore the arch wire can easily be displaced from the arch wire slot.

U.S. Pat. No. 4,492,573 to Hanson improved upon the original design by 1) bending the free end of the retainer member's labial side so that it can be inserted into the arch wire slot, 2) adding a mesial-distal retainer slot to the gingival side of the arch wire slot and 3) forming a saddle ridge at the labial side of the body. The first two modifications help to hold the free end of the clip's labial side at closed position and prevent the clip from moving beyond its elastic limit when subjected to a force in the labial direction. The third secures the clip's labial side at the open position. However, there is still insufficient restraint on the free end of the clip's labial side when it is subjected to a force in the mesial-distal direction.

U.S. Pat. No. 5,586,882 to Hanson documented the use of a Ni—Ti based shape-memory alloy as the clip material. Self-ligating orthodontic brackets comprise a U-shape spring clip with converging arms movable on the bracket body between slot open and closed positions; in the latter position the spring retains an arch wire in the slot and urges the bracket and wire to their optimum relative positions. The clip is of a superelastic shape recovery metal alloy, preferably of thickness from 0.20 mm (0.008 in) to 0.25 mm (0.010 in), with rounded edges.

The original design by Hanson did not have a restraint to prevent clip moving in the mesial-distal direction. U.S. Pat. No. 5,906,486 to Hanson added a cut-off in the gingival side of the arch wire slot wall to retain the clip and prevent it from moving in the mesial-distal direction. The free end part of the labial arm portion extends into the recess to protect the spring member against excessive movement in the labial direction. Brackets based on the design concepts disclosed in the above patents have been marketed by Speed System and still available today. Only metal brackets have been produced and no aesthetic version is available.

A hybrid between a conventional twin bracket and a flexible clip active self-ligating bracket, known as the In-Ovation bracket, was developed by Voudouris in 1997 and is described in U.S. Pat. No. 5,857,850. An improved design has been available since 2002, marketed as In-Ovation R (See U.S. Pat. No. 6,368,105 and U.S. Pat. No. 6,776,613). An important feature of the design is a slot blocker to prevent the clip's movement in the m-d direction. An aesthetic version of this system (In-Ovation C) was introduced in 2007 in the form of a ceramic bracket, in which the metal clip has been plated with Rh so that it is matte in appearance and thus does not reflect light as much as a polished surface would. The clip is made of a Co—Cr—Mo alloy and tends to lose its modulus after use during treatment. However, the coating tends to wear off in the early stage of treatment and lose its aesthetics.

SUMMARY OF THE INVENTION

It is therefore an object of the invention to develop a self-ligating orthodontic bracket that is easy to use, securely fastened and aesthetically pleasing.

These and other objects are accomplished by an orthodontic bracket comprising a base configured for attachment to a tooth surface, a bracket element with an arch wire slot attached to one side of the base, and a clip for securing the arch wire in the slot. The arch wire slot is formed in a labial side of the bracket element and runs along a mesiodistal direction of the bracket element.

The bracket element has a wall portion extending upward along one side of the arch wire slot. This wall portion has three indentations in a line parallel to the mesiodistal direction. There is a channel running entirely through the bracket element underneath the arch wire slot and in a gingival-occlusal direction of the bracket.

The clip is substantially U-shaped and has a first end with three parallel protrusions shaped to fit within the three indentations of the wall portion, and a second end having a locking element. The clip is securable to the bracket by placing the second end through the channel and engaging the locking element onto the bracket element, and placing the protrusions into the indentations of the bracket element. The protrusions are held in the indentations by friction due to the downward spring force of the clip on the floor of the indentation. The clip is releasable by sliding the protrusions out of the indentations to expose the arch wire slot.

The combination of the three protrusions and three indentations secures the clip firmly when it is subjected to force in the mesial-distal direction and provides an even distribution of forces on the arch wire during the active ligation stage.

The locking element can be a notch on an exterior surface of the clip, the notch engaging a stepped wall of the channel to keep the clip in the channel. Other locking arrangements could be used as well.

In one embodiment, the clip is made of a Ni—Ti alloy. This alloy exhibits superelasticity, which keeps the elastic modulus of the clip substantially unchanged even with extended use. The clip can also be coated with a coating such Au/Rh, Pt/Rh and Pd/Rh, with Rh being an outermost layer. This coating minimizes the amount of Ni that leaches from the clip, and improves the aesthetics of the bracket when used in conjunction with a ceramic bracket body.

In a preferred embodiment, the arch wire slot is chamfered on its edges to minimize friction when inserting and removing the arch wire from the slot.

Preferably the base is manufactured by embossing protrusions into the base, by stamping the base immediately after molding. This forms undercuts around the protrusions, which enhances the adhesion of the base to the tooth surface.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
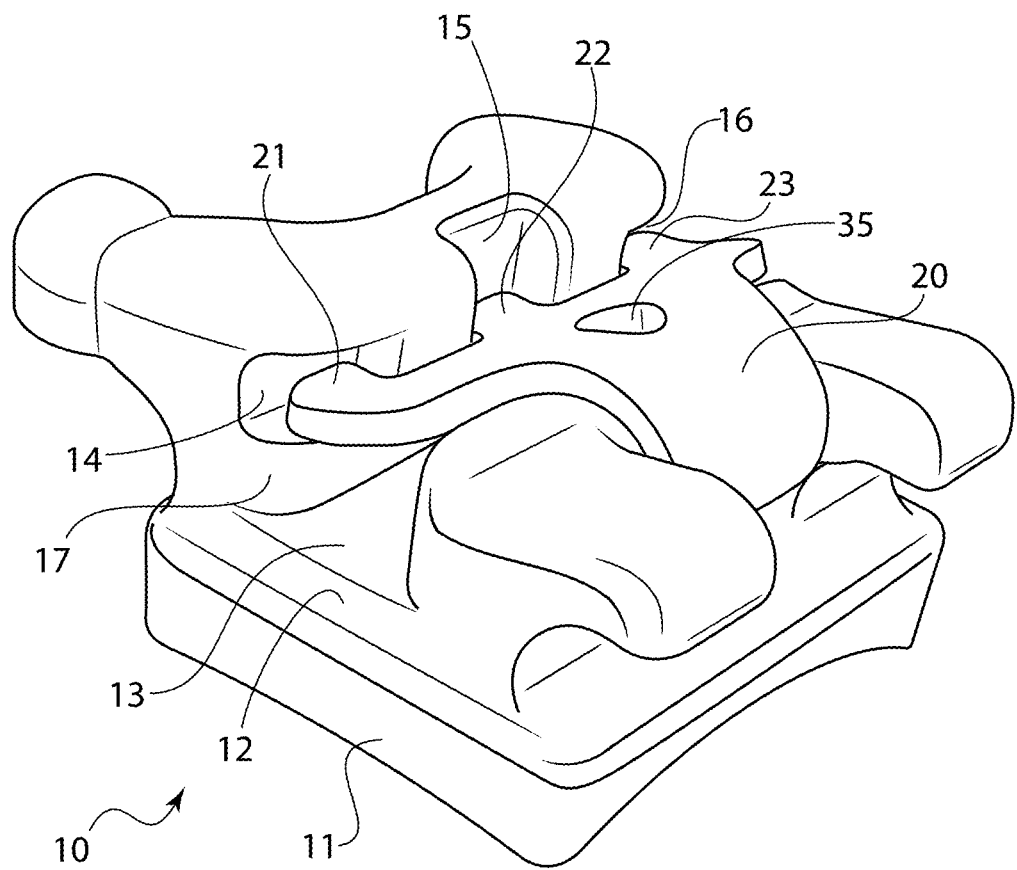
FIG. 1 shows a perspective view of the bracket according to the invention.
Figure 2:
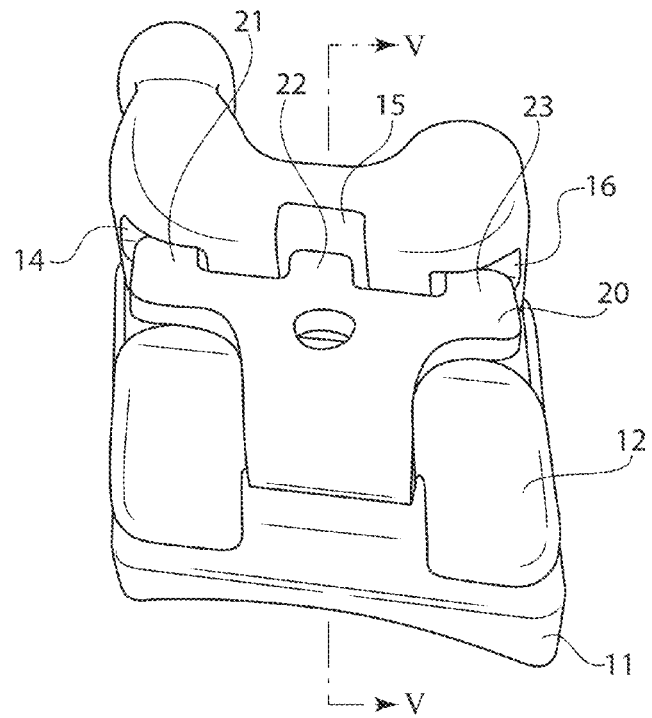
FIG. 2 is a top view thereof.
Figures 3, 4:
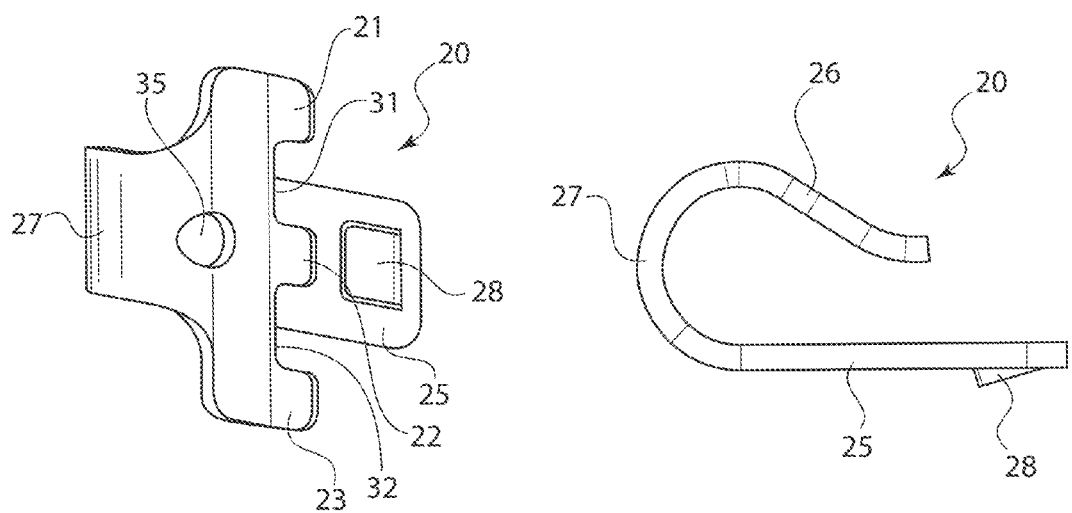
FIG. 3 is a top view of the clip according to the invention.
FIG. 4 is a side view of the clip.

Referring now in detail to the drawings, FIGS. 1 and 2 show a self-ligating orthodontic bracket 10 comprising a base 11 and a bracket element 12, as well as a U-shaped ligating clip 20, shown in detail in FIGS. 3 and 4. Bracket element 12 has a mesial-distal slot 13 to accept an arch wire. Three cavities 14, 15, 16 are made at the gingival wall 17 of slot 13. Clip 20 has a first end with three protrusions 21, 22, 23 which engage indentations 14, 15, 16 when the clip 20 is in the closed position. This three-protrusion/three-indentation combination secures the clip firmly when it is subjected to force in the mesial-distal direction, providing an even distribution of forces on the arch wire during the active ligation stage. The three-protrusion/indentation formation provides substantially better distribution of force as compared with standard two-protrusion/indentation brackets. Clip 20 can be slid open and closed with the aid of an aperture 35 disposed behind protrusions 21, 22, 23. A user can slide clip 20 open and closed by inserting a tool through aperture 35 and moving the tool back and forth.

The clip 20 is made of a superelastic material. The bracket element and base can be made of ceramics, metals, or polymeric materials.

Figure 5:
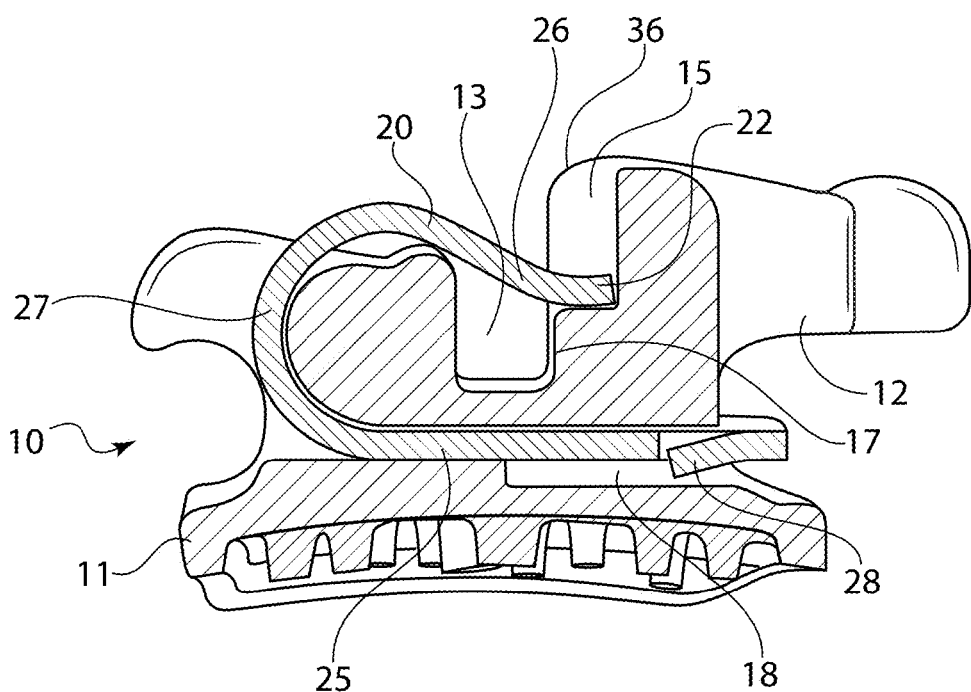
FIG. 5 is a cross-sectional view along liens V-V of FIG. 2.

As shown in FIG. 5, lingual side 25 of clip 20 is inserted into a gingival-occlusal channel 18 of bracket element 12 and the labial side 26 is used for locking and unlocking the arch wire slot 13. The two sides are connected by a bend 27 at the gingival side. The lingual side 25 and the bend 27 are narrower than the width of the channel 18, so that the clip 20 can be easily inserted.

At the labial side 26, the clip 20 expands to cover the full length of the arch wire slot towards its gingival end. Two cut-outs 31, 32 are made at free gingival end of the clip to form the three parallel protrusions 21, 22, 23. The protrusions are angled so that they are parallel to the lingual side 25 of the clip 20.

As shown in FIGS. 3-5, a notch 28 is cut out at the center of the lingual side 25 to serve as a locking tab so that clip 20 will not separate from the bracket element 12 after being inserted into the channel 18. Channel 18, as shown in FIG. 5, has two stepped sections: the section 33 at the gingival side has a higher clearance to allow the notch 28 to slide freely and the other section 34 with a lower clearance to stop the notch 28. The location of the stepped divide between the two sections is determined so as to minimize the length of the lingual side portion of the clip and not extend far beyond the bracket base boundary.

Figure 6:
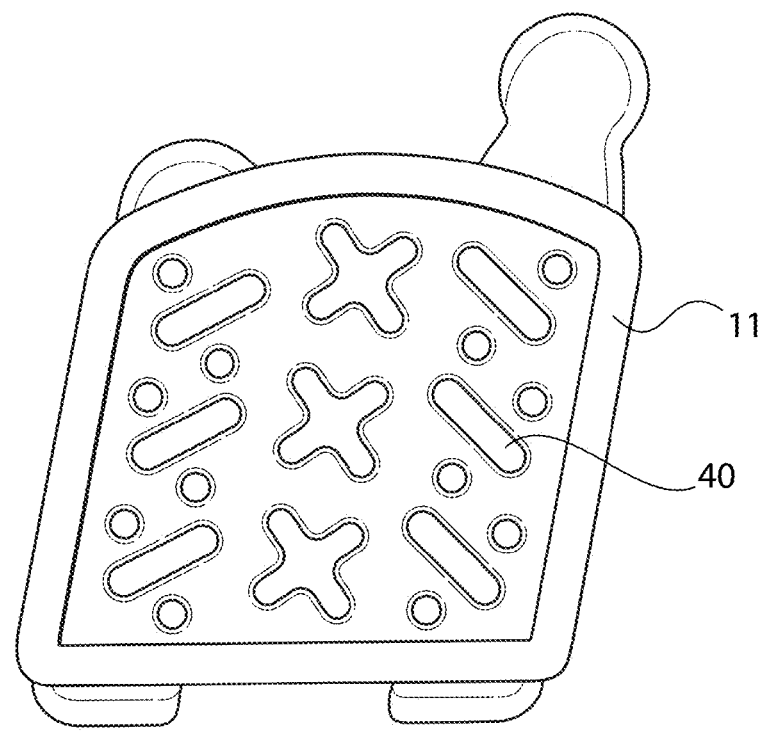
FIG. 6 is a bottom view thereof.
Figure 7:
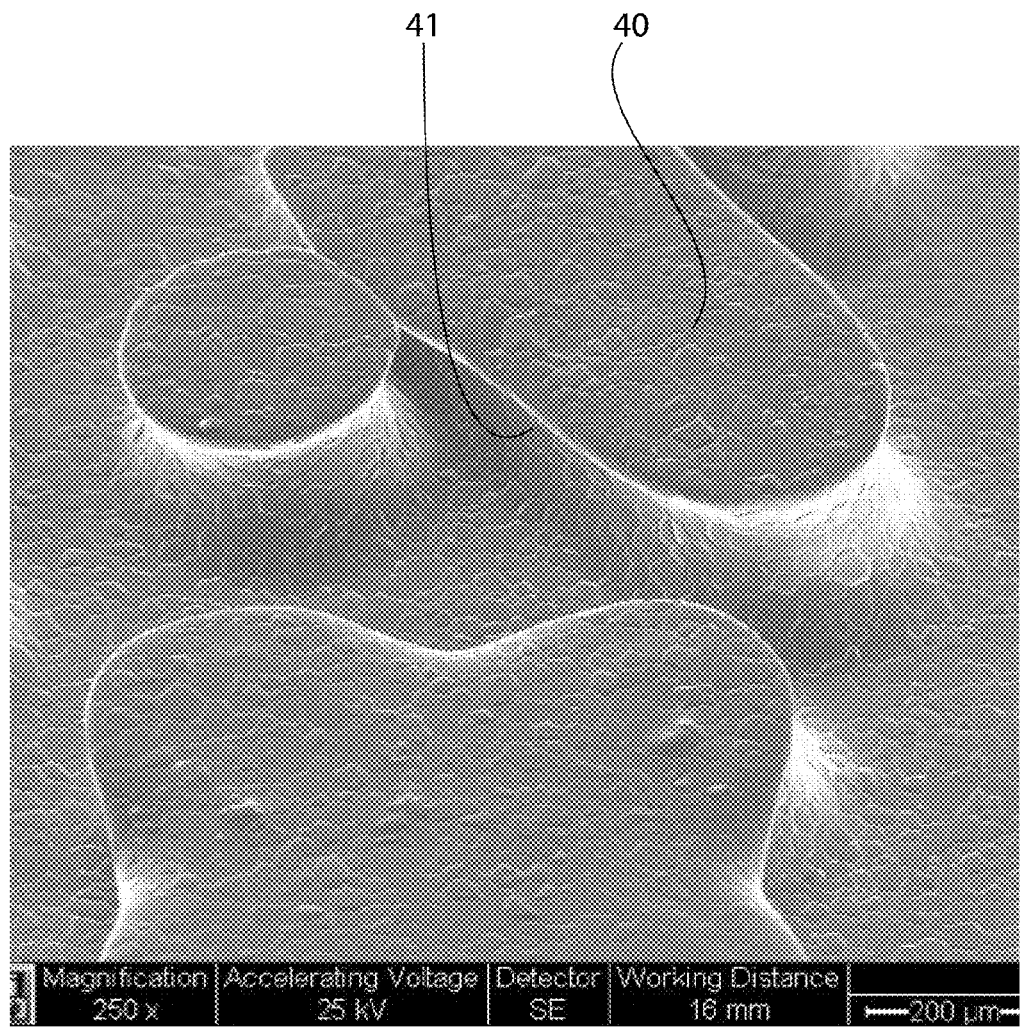
FIG. 7 is a photograph of the bottom view, showing the formation of undercuts in the protrusions.

The base 11 is bonded to the tooth enamel by applying adhesives between the base and enamel. A structured bottom surface of the base 11 can be formed such as shown in FIG. 6. No adhesion promoter is applied on the surface of the base 11 to enhance bonding chemically, and the bonding to the base is completely mechanical by anchoring solidified adhesives at undercuts on the base, formed either by embossed protrusions or particles glued to the base. A shown in FIG. 6, protrusions 40 are embossed over the surface of the base 11. Undercuts 41, as shown in FIG. 7 are formed by stamping the protrusions 40 right after the molding process, simplifying the manufacture process and lowering its cost.

In a preferred embodiment, the clip 20 is made of Ni—Ti alloy. Due to the superelastic property of the alloy, the elastic modulus of the clip remains unchanged even after extended use in oral cavity. This is a big advantage compared with other spring materials such as Co—Cr—Mo alloys. In addition, the clip can be coated with dual layers of Au/Rh, Pt/Rh or Pd/Rh, all with Rh in the outermost layer. Preferably, the thickness of the Rh is between 0.5 µm and 3 µm to maintain the integrity of the coating during long exposure in oral cavity. This coating can minimize Ni from leaching and improve the esthetics when used along with a ceramic bracket body.

In another preferred embodiment, the bracket body is manufactured by injection molding. The molded green bodies are converted to transparent ceramics through binder burnout, sintering and/or hot isostatic pressing. The materials can be high-purity alumina, zirconia or other compounds that can be densified to full density and high translucency, such as sialon or spinel. Preferably, the body is polished chemically to produce a fine surface finish. The smoothly polished surface, combined with a chamfer 36 at the edge of the arch wire slot (FIG. 5), make friction of arch wire over the slot extremely small. The frictional force can be comparable to or even smaller than that over a polished metallic bracket.

Accordingly, while only a few embodiments of the present invention have been shown and described, it is obvious that many changes and modifications may be made thereunto without departing from the spirit and scope of the invention.

What is claimed is:

1. An orthodontic bracket comprising:

a base configured for attachment to a tooth surface;

a bracket element attached to one side of the base, the bracket element comprising:

an arch wire slot formed in a labial side of the bracket element and running along a mesiodistal direction of the bracket element, said arch wire slot being configured for supporting an arch wire therein;

a wall portion of the bracket element extending upward along one side of the arch wire slot, the wall portion having three indentations in a line parallel to the mesiodistal direction; and a channel running entirely through the bracket element underneath the arch wire slot and in a gingival-occlusal direction of the bracket; and a substantially U-shaped one-piece clip having a first end with three parallel protrusions shaped to fit within the three indentations of the wall portion, and a second end having a locking element;

wherein the clip is securable to the bracket by placing the second end through the channel and engaging the locking element on a gingival side of the bracket element and placing the protrusions into the indentations of the bracket element, wherein the protrusions are held in the indentations by downward spring force of the clip, and wherein the clip is releasable by sliding the protrusions out of the indentations to expose the arch wire slot.

2. The bracket according to claim 1, wherein the locking element is a notch on an exterior surface of the clip, wherein the channel is formed from two stepped sections, and wherein the notch engages a wall of one of the sections to maintain the clip in the channel.

3. The bracket according to claim 1, wherein the clip is made of a Ni—Ti alloy.

4. The bracket according to claim 2, wherein the clip is coated with a material and is selected from the group consisting of Au/Rh, Pt/Rh and Pd/Rh, with Rh being an outermost layer.

5. The bracket according to claim 1, wherein the arch wire slot is chamfered at its edges.

6. The bracket according to claim 1, wherein the bracket element and base are formed of ceramic.

7. The bracket according to claim 1, further comprising an aperture in the clip for receiving a tool to slide the clip between an open and a closed position.

\* \* \* \* \*